United States Patent
Gombinski (12)

(10) Patent No.: US 6,297,062 B1
(45) Date of Patent: Oct. 2, 2001

(54) SEPARATION BY MAGNETIC PARTICLES (75) Inventor: Moshe Gombinski, Bat-Yam (IL)

(73) Assignee: Bio-Magnetics Ltd., Ariel (IL)

( * ) Notice: Subject to any disclaimer, the term of this patent is extended or adjusted under 35 U.S.C. 154(b) by 0 days.

(21) Appl. No.: 09/034,209

(22) Filed: Mar. 4, 1998

Related U.S. Application Data (63) Continuation-in-part of application No. 08/811,016, filed on Mar. 4, 1997, now abandoned.

(30) Foreign Application Priority Data

Mar. 7, 1996 (IL) .......................................... 117393

(51) Int. Cl.$^7$ .......................... G01N 33/553; G01N 33/53
(52) U.S. Cl. .......................... 436/526; 436/528; 436/529; 436/531; 436/533; 436/535; 436/538; 436/541; 436/542; 436/807; 436/808; 436/809; 436/810; 436/501; 436/824; 436/518; 435/6; 435/7.1; 435/7.2; 435/7.5; 435/7.8; 435/4; 435/173.1; 435/7.92; 435/7.9; 435/973; 435/975
(58) Field of Search ..................................... 436/526, 533, 436/528, 529, 531, 535, 538, 177, 178, 541, 542, 807, 808, 809, 810, 824, 501, 518, 524; 435/6, 7.1, 7.2, 7.5, 7.8, 4, 173.1, 7.92, 7.9, 973, 975; 424/1.25, 1.21; 422/101

(56) References Cited

U.S. PATENT DOCUMENTS

| | | | |
|---|---|---|---|
| 3,970,518 | * 7/1976 | Giaever | 195/1.5 |
| 4,169,804 | 10/1979 | Yapel, Jr. | 252/62.53 |
| 4,230,685 | * 10/1980 | Senyei et al. | 424/12 |
| 4,554,088 | 11/1985 | Whitehead et al. | 252/62.54 |
| 4,666,595 | * 5/1987 | Graham | 210/222 |
| 4,677,067 | * 6/1987 | Schwartz et al. | 435/177 |
| 4,745,077 | * 5/1988 | Holian et al. | 436/526 |
| 4,988,618 | * 1/1991 | Li et al. | 435/6 |
| 5,108,704 | * 4/1992 | Bowers et al. | 422/70 |
| 5,256,532 | * 10/1993 | Melnicoff et al. | 435/6 |
| 5,395,498 | 3/1995 | Gombinsky et al. | 204/182.8 |
| 5,567,326 | * 10/1996 | Ekenberg et al. | 210/695 |
| 5,646,001 | * 7/1997 | Terstappen et al. | 435/7.21 |
| 5,646,263 | * 7/1997 | Ekenberg et al. | 536/25.4 |
| 5,693,784 | * 12/1997 | Ekenberg | 536/25.4 |
| 5,779,907 | * 7/1998 | Yu | 210/695 |
| 5,837,860 | * 11/1998 | Anderson et al. | 536/25.3 |

OTHER PUBLICATIONS

Morag, Ely et al., "Immobilized Nitro–avidin and Nitro–streptavidin as Reusable Affinity Matrices for Application in Avidin–Biotin Technology," *Analytical Biochemistry*, vol. 243, Article No. 0514, 1996, pp. 257–263.

(List continued on next page.)

*Primary Examiner*—Long V. Le
*Assistant Examiner*—Pensee T. Do
(74) *Attorney, Agent, or Firm*—Oliff & Berridge, PLC (57) ABSTRACT The present invention concerns a method for separating at least one species of biological entities from a sample solution, by contacting the sample with a matrix of magnetic particles formed on a substrate such as a sheet a gel, etc. The particles in the matrix are coupled to entities capable of specifically binding to the species of biological entities to be separated. The separation is carried out either for detection purposes for obtaining separately each species of biological entities or for synthesis purposes. The invention further concerns matrices of magnetic particles formed on various substrates and kits for use in the method.

15 Claims, 5 Drawing Sheets

OTHER PUBLICATIONS

Valerio, Robert M., "Synthesis of Peptide Analogues Using the Multipin Peptide Synthesis Method," *Analytical Biochemistry*, vol. 197, 1991, pp. 168–177.

Jacobs, Jeffrey W. et al., "Combinatorial chemistry—applications of light–directed chemical synthesis," *TIBTECH*, vol. 12, Jan. 1994, pp. 19–24.

Pourfarzaneh, M. et al.; "The Use of Magnetizable Particles in Solid Phase Immunoassay"; Methods of Biochemical Analysis; 28:267–295 (1982).

Kafatos, F.C. et al.; Nucleic Acids Research, 7:1541–1552 (1979).

Richard Hawkes et al.; "A Dot–Immunobinding Assay for Monoclonal and Other Antibodies"; Analytical Biochemistry; 119:142–147 (1982).

Pappas, M.G. et al.; "Dot Enzyme–Linked Immunosorbent Assay (Dot–ELISA): a Micro Technique for the Rapid Diagnosis of Visceral Leishmaniasis"; Journal of Immunological Methods; 64:205 (1983).

Drmanac, R. et al.; "Sequencing by hybridization: Towards an automated sequencing of one million M13 clones arrayed on membranes"; 13:566–573 (1992).

Mirzabekov, A. D.; "DNA sequencing by hybridization—a megasequencing method and a diagnostic tool?"; 12:27–32 (1994).

Hultman, T. et al.; "Bidirectional Solid–Phase Sequencing of In Vitro–Amplified Plasmid DNA"; 10 (1):84–93, (1991).

* cited by examiner

SEPARATION BY MAGNETIC PARTICLES

This is a Continuation-in-Part of application Ser. No. 08/811,016 filed Mar. 4, 1997, now abandoned. The entire disclosure of the prior application is hereby incorporated by reference herein in its entirety.

FIELD OF THE INVENTION

The present invention concerns a method for separating and detecting biological molecules, utilizing magnetic particles. The present invention fur tier concerns products, and kits used in said method, as well as methods for the preparations of said products.

BACKGROUND OF THE INVENTION

Magnetic particles are used for a variety of separation, purification, and isolation techniques in connection with biological biomolecules. In those techniques, a magnetic particle is coupled to a molecule capable of forming a specific binding (hereinafter "affinity binding") with a molecule in a biological sample, which is to be isolated, purified or separated. The biological sample is then brought into contact with the magnetic particle and those biological molecules which bind to the magnetic particle are then isolated by application of a magnetic field.

Such magnetic separation techniques have been employed to sort cells, to recover antibodies or enzymes from a solution, to purify proteins using affinity techniques, and to remove unwanted particles from suspension, for example, to remove cancer cells ex vivo, from a cell preparation which is then injected into a patient (Pourfarzaneh, M. et aL, "The use of magnetizable particles in solid phase immunoassay in methods of biochemical analysis" 28:267–295 (1982)).

U.S. Pat. No. 4,554,088 discloses a process for the preparation of magnetic particles, capable of coupling to a wide variety of molecules. The magnetic particles are then dispersed in an aqueous media without rapid settling, and can conveniently be reclaimed from the media using a magnetic field.

U.S. Pat. No. 4,169,804 discloses a magnetically responsive composite microparticle comprising a magnetically responsive material and a porous solid water-insoluble matrix such as proteinaceous material, polysaccharides and the like. The magnetically responsive material is dispersed throughout the permeable, solid, water insoluble matrix. The microparticles of this U.S. patent, are intended to substitute microparticles in labeling or for the purpose of carrying medicaments and drugs, since due to their magnetic responsiveness, they can be easily retrieved or relocated without the need to employ expensive equipment The microparticles are also used as vectors in chemical reactions, and in determining levels of biological compounds in a sample.

Separation, isolation and purification techniques utilizing magnetic particles, are used to separate or isolate a single species of molecules from a sample at a time, depending on the nature of the molecule coupled to the magnetic bead. Prior art methods, do not disclose methods for separating several molecular species from a sample simultaneously.

U.S. Pat. No. 5,395,498 discloses a method for obtaining molecules which are separated on an electrophoretogram. Said electrophoretogram is then brought into contact with a matrix of magnetic particles having binding specificity to one or more biological molecules present on the electrophoretogram, whereby these molecules bind to the magnetic particles in the matrix. The particles can then be collected on the basis of their magnetic properties, and by this the electrophoretically separated molecules can be obtained. Although this U.S. patent discloses a method suitable for obtaining several different species of biological molecules simultaneously utilizing magnetic means, it concerns only molecules separated on electrophoretograms, and does not concern at all molecules present in a liquid sample.

It would have been highly desirable to provide a method, and means for a simultaneous separation and isolation of several different species of biological molecules from a liquid sample without the step of electrophoretic separation.

Blotting techniques, were initially constructed for transferring DNA patterns from electrophoretic agarose gel to nitrocellulose membrane filters. A modification of the blotting technique termed "dot hybridization method" F. C. Kafatos, Nuc. Acids. Res., 7:1541–1552 (1979)) was developed, in which, instead of being blotted from a gel to the filter, the probe is applied directly to the nitrocellulose filter at a discrete spot. Such a construction allows considerable simplification of the detection procedure and simultaneous screening of a large number of samples. An analogous protocol for antigen-antibody reaction termed "dot immuno binding" was described by Richard Hawkes (Anal Bio 119:142–147 (1982)) for applications such as screening of hybridoma clones, where a large number of samples must be screened for a specific antibody, and for a diagnostic procedure by which a large number of antibodies may be assayed simultaneously. A modification of the dot immuno binding termed "dot-ELISA" (dot-enzyme-linked immunosorbent assay) was described by M. G. Pappas (J. Immun. Mth, 64:205 (1983)). Dot-ELISA combines the advantages of both the above methods and can be compared in sensitivity to radioimmunoassay.

Commercial equipment for dot immuno-binding such as the Bio-Dot™ and the Bio-Dot SF™ (Slot Format) microfiltration units from Bio-Rad (ISA) provide a reproducible method for binding proteins or nucleic acids present in liquid solutions onto nitrocellulose or Zeta-Probe™ (Bio-Rad, U.S.A.) membranes. The disadvantage of such equipment, and similar equipments, resides in the necessity for manual handling, which requires, for example, manual pipettes to apply the samples onto the membranes.

Biomek 1000™ (Beckman, USA) is a robotic work station which enables automization of procedures for DNA hybridization. It consists of two different devices for creating dots on a filter sheet: a dot-blotting apparatus and a high density replicating (HDR) system designed to allow the replication of a large number of bacteria, phage or DNA samples from a microtiter plate to a single filter. The precision of the Biomek allows to produce samples in a grid format, with high reproducibility. The high density replicating system uses a 96-pin tool in order to transfer the samples from the microtiter plate to the suitable substrate which may be agar or membrane. The equipment is automatically cleaned and sterilized between each successive transfer of 96 samples from the microtiter plate. Samples from up to 36 microtiter plates can be transferred to a single substrate.

The robotic station Biomek 1000™ is adapted for high density spotting (Dramanac et al, Electrophoresis, 13:566–573 (1992)).

"Sequencing by hybridization", refers to a technique for sequencing an unknown stretch of oligonucleotides, by determining whether it can form a mismatch-free hybridization with a series of shorter known sequences, termed "probes". Technically, sequencing by hybridization (SBH) can be performed in two formats, with either the DNA or the short oligonucleotide probes immobilized to a solid support. In the first format, the probes are labeled by individual detectable labels, and hybridize to a genomic DNA immobilized to the support. In the second format, genomic fragments of appropriate length are appropriately labeled, and for each of them a separate hybridization reaction with immobilized probes is carried out. The first format, is technically carried out by a dot-blot hybridization system using Beckman's commercial HDR system or similar commercially available systems. The second format is carried out by a technically different variant system, capable of spotting synthesized oligonucleotides on glass covered by activated acrylamides, and direct parallel synthesis of oligonucleotide by physical masking, by photolithography, or by a combination of synthesis of oligonucleotides on microbeads and formation of a fixed bead monolayer. A solid support with samples which may be either the short probe oligonucleotides or genomic DNA samples, spaced on a micrometer scale, has been termed "a sequencing chip".

One of the most severe problems in both formats of sequencing by hybridization technique is the time consuming step of washing of the filters. In order to permit multiple usage of the filters it is necessary to strip off the probes again and again. The major technical problem with the method is to obtain scorable hybridizations with most of the probes over most of the clones. If half a filter is unsuccessful, the whole filter must be repeated. Accuracy of the hybridization data is also a problem and the error rate could be increased from 3% due to higher dot density and uneven hybridization on larger filters.

It would have been highly desirable to provide techniques which would aid in sequencing reduction of costs and time concerned with SBH methods. "Combinatorial chemistry" is a term used for chemical and biological synthesis techniques intended to produce molecules having a huge diversity. In biology, molecular libraries of diverse biological molecules, such as peptides, are created by the random and controlled assembly of a basic set of smaller molecular substituents termed "building blocks". The building blocks may be single amino acids or sequences of short peptides.

A very widely used technique of combinatorial chemistry is termed "divide and pool". In this method peptide-synthesis beads are segregated into individual reaction vessels for the coupling of specific amino acids, the beads are then combined, mixed to homogeneity and redivided into separate reactions vessels for the subsequent coupling step. A distinct advantage of this method is that a potentially unlimited number of monomers may be used in the combinatorial assembly of the library, creating a huge number of diverse peptides which may be later surrendered for their activity (Jacobes W. Jeffrey and Fodor P. A. Stephen *Tibtech*, Jan. 1994 12: 1994). A major problem in the combinatorial chemical synthesis of biological molecules is the need for individual purification of each molecule produced which is labor and time consuming. An attempt to solve this problem was by the use of a multi-pin assembly (96-pin format for example of chiron memitops) in which the generated molecules were covalently bound to the plastic pins allowing repetitive assays to be performed (Valerio et al., *Anal. Biochem.*, 197:168–177 (1991)).

GLOSSARY

The following terms may be used throughout the specification.

Biological entities—concerns any type of molecules, complexes of molecules or cells present in biological tissues such as proteins, DNA, RNA, hormones, enzymes, receptors, ligands, polysaccharides and the like, as well as molecules which are laboratory produced and which are intended to be similar to biological molecules obtained from a natural source, such as laboratory produced and synthesized peptides, or oligonucleotides, antibiotics, and the like. The term biological entities also concerns cells, virions, plasmids, various cell organels (mitochondira, nuclease, etc.).

Sample—Any type of liquid media containing the biological entities, which are to be isolated, separated, or detected.

Magnetic particles—particles of various sizes, comprising a magnetic substance, being a substance which is either a magnet, i.e. having a 'magnetic memory' or a substance which is not a magnet but is attracted to magnets, i.e. a ferromagnetic material. The magnetic particles may consist solely or essentially of the magnetic substance. Alternatively, the magnetic particles may be composite particles comprising the magnetic substance and other non-magnetic substances such as agar, agarose, non-magnetic metal, glass, nitrocellulose, etc. The composite particle may either consist of a core or be made of the magnetic substance and a shell made of the non-magnetic substance or may comprise several sub-particles made of the magnetic substance embedded in the non-magnetic substance. The term "magnetic particles" is to be understood as encompassing also the so-called "magnetic beads" or "magnetic microbeads" used in the literature.

The use of magnetic particles in which the magnetic substance is ferromagnetic is generally preferred, for example, particles made of superparamagnetic iron oxide. Such particles are capable of responding well to relatively weak magnetic fields, but have essentially no magnetic memory, that is once the magnetic field is removed they do not maintain magnetic attraction forces.

Coupled—the link between the magnetic particle and the second member of the pair forming group (see below). Such a link can be carried out by any method known in the art, for example, by coating the magnetic particle with said second member. The coupling may also be carried out by forming composite particles, for example, agarose particles comprising both the ferromagnetic material (i.e. magnetic particles) and the second member of the pair forming group.

Pair forming group—two biological entities, capable of affinity binding (hereinbelow) to each other. Examples of pair forming groups are: two complementary DNA sequences, two complementary RNA sequences, a complementary DNA and RNA sequence, an enzyme and its substrate, an antibody and its antigen, a receptor and its ligand, an enzyme and its substrate, a lectin and its specific glycoprotein, streptavidin and biotin, a virion and an antibody capable of recognizing one of its membranal proteins, and the like. Each member of the pair forming group is capable of distinguishing the other member of the pair forming group from among similar biological entities and specifically binding thereto.

A first member of a pair forming group or first member—one member of the pair forming group of above, which is present in the sample and is to be isolated, purified or detected.

A second member of a pair forming group or second member—the second member of the pair forming group capable of affinity binding (see below) to the first member. Said second member is coupled to the magnetic particle.

Affinity binding—the attractive and binding forces between two members of a pair forming group.

Matrix of magnetic particles or matrix—a predetermined spatial arrangement of magnetic particles, in a specific pattern (discreet dots, lines, strips, etc.) on a desired substrate (see hereinbelow).

Matrix of magnets—a predetermined spatial arrangement of magnets in a specific pattern formed on a flat surface usual corresponding to the pattern of the matrix of magnetic particles.

Substrate—a media which carries the matrix of magnetic particles. The substrate may be a membrane (see hereinbelow) on which the particles are adhered by absorption or adsorption; a gel where the particles are present on its outer face or immobilized at some distance inside the gel; a solid surface such as a glass, plastic or metal plate on which the magnetic particles are present and in such a case the magnetic particles are immobilized on the solid surface by placing magnets on the other side of the surface. The solid surface itself may be a magnet. Alternatively, the substrate may be an array of small liquid-holding wells, each well containing magnetic particles, which array is placed on a magnet or an array of magnets.

Membrane—a thin soft pliable sheet or layer capable of retaining the magnetic particles examples being nitrocellulose sheet, pergamenous sheet, polycarbonate, cellulose acetate sheet, xerographic paper, etc.

Species of biological entities—one type of biological entity, for example, a specific sequence of DNA, a specific protein or polypeptide, one type of monoclonal antibody, one variety of bacteria and the like.

SUMMARY OF THE INVENTION

The present invention provides a method for isolating one or more species of biological entities, each species being a first member of a pair forming group, from a sample solution by contacting the sample solution with a matrix of magnetic particles wherein each magnetic particle in the matrix is coupled to the second member of the pair forming group. Preferably, the matrix should contain magnetic particles, coupled to several different species of second members of the pair forming groups, for example, to different types of antibodies, wherein all the magnetic particles which are coupled to a specific species of said second member are present in a discreet location in the matrix, which is different than the location of the other magnetic particles. When the sample is contacted with said matrix, and each species of biological entities, (first member of the pair forming group, for example, a specific antigen) binds to its specific second member of the pair forming group (for example its specific antibody) which is present in a discrete location in the matrix. Thus each species of the biological entities is spatially separated, in a discrete location, from the other entities, and due to the magnetic properties of the magnetic particles, each species may be obtained separately.

The present invention enables to carry out multiple separations and isolations of biological entities simultaneously, using a single matrix, either to separate several different species of biological entities from a single sample or to separate the same species of biological entities from a plurality of different samples at once.

Thus, the present invention provides a method for separating at least one specific species of biological entities, which constitute a first member of a pair forming group, from a sample comprising:

contacting the sample with a matrix of magnetic particles formed on a substrate, the particles being coupled to at least one species of the second member of the pair forming group which specifically binds to said at least one species of biological entities.

Preferably where the matrix comprises magnetic particles coupled to more than one species of the second member of the pair forming group, all particles coupled to the same species are present at the same location in the matrix, which location is discrete from the location of magnetic particles coupled to other species of the second member.

The method for separation of the present invention, may be used for detection purposes only, and in such a case, it comprises a further step of processing the matrix of magnetic particles, (which are affinity bound to the specific species of biological entities which were separated from the sample), in order to produce a detectable label. For example, such processing may be carried out by adding an antibody capable of yielding a color reaction, or bearing a fluorescent or radioactive moiety, which is capable of specifically binding to the species of the biological entities which were separated on the magnetic particles. Where the matrix of magnetic particles consists of more than one species of the second member of the pair forming group coupled to the magnetic particles, and each species of said second member is present in a discrete location in the matrix, the matrix can be processed to give a different detectable signal for each species. This can be done, for example, by immersing the matrix in a mixture of different antibodies, each type of antibody capable of specifically binding to a different species of biological entities, and giving a different detectable signal. Alternatively, it is possible to use only a single type of antibody (such as anti-IgG antibody) and to detect the presence of the various species of biological entities by determining to which discrete location in the matrix these antibodies are bound.

By using the method of the invention for detection purposes, it is possible to utilize a single matrix of magnetic particles in order to detect simultaneously the presence of several different species of biological entities in the sample, and if the detectable signal can be calibrated, it is even possible to determine the level of these species of biological entities in the sample.

Another type of determination may be carried out by using magnetic particles all of which are coupled to the same species of the second member of the pair forming group, these particles being arranged in a specific pattern in the matrix. For example, the magnetic particles may be arranged in a 96-dot arrangement corresponding in pattern to the 96-pin device and 96-well format and piptor suitable for this format. Such a matrix enables to deposit or blot on each dot of magnetic particles a different sample and then detect at once, by suitable processing, which dot is bound to a specific biological entity. If desired, it is possible to shift the 96-peptide a few micrometers and create a new 96-dot pattern in the same area of membrane. By repeating the shifting several times, it is possible to create an arrangement of several thousands of dots in a small area of membrane of several sq. cm.

Another approach is to use an array of small wells each holding a liquid and magnetic particles which array is present on a magnet. The determination can be carried out separately and simultaneously in each well.

Alternatively, or in addition to detection purposes, the method of the invention may be utilized to physically obtain the various species of biological entities separated from the liquid sample. Due to the magnetic properties of the particles, it is possible to collect them using a magnetic force. If it was desired to separate one species of biological entities from a single sample, then all magnetic particles present on the matrix are collected. However, preferably the matrix should contain magnetic particles coupled to several species of the second member of a pair forming group, each species capable of specifically binding to a different species of a first member of a pair forming group and each species present in a discrete location on the matrix. For example, the matrix may be arranged in dots, wherein the first dot bears the magnetic particles coupled to an antibody against protein A, the second dot to an antibody against protein B, the third dot to an antibody against protein C, etc. By separately collecting first, second and third dots into separate vessels, and optionally separating the bound protein from its antibody, it is thus possible to obtain simultaneously several different species of biological entities utilizing a single matrix. The magnetic particles bound to different species of second members may also be formed in a 96-dot form as explained above where each dot (or several dots) is composed of magnetic particles of a different species. The magnetic particles may also be in an arrangement of liquid-containing wells, for example, a 96 arrangement of wells and magnetic particles may be separately obtained from each well.

Another use of the method of the invention is by what is termed "Sequencing by Hybridization" (SBH). Sequencing via hybridization is specified in Miizabekov A. D., *Tibtech*, 12:27-32 (1994) and generally concerns a technique wherein the sequences of long stretches of nucleic acids are determined by sequentially selecting only those sequences which hybridize with smaller, known nucleic acid sequences termed "probes". Therefore, it is possible to utilize the method of the invention for determining the sequence of a long nucleic acid sequence coupled to a magnetic particle. The long sequence is sequentially incubated with known nucleic acid "probes", wherein each probe bears a different detectable label. Those magnetic particles coupled to sequences which show hybridization to the first probe are separated from the matrix. The magnetic particles thus obtained are rearranged in a second matrix and then incubated with a second probe. Again, all the magnetic particles coupled to sequences which were capable of binding also to the second probe are collected and rearranged in a third matrix of magnetic particles. These steps are repeated again and again and in each time only those magnetic particles coupled to nucleic acid sequences capable of hybridizing to the new probe are obtained so that eventually there remains only magnetic particles carrying sequences which were able to hybridize to all the probes used. Since the sequences of the probes are known it is thus possible to determine the long sequence to which all the probes hybridized.

Still another use of the method of the invention is for synthesis of biological molecules, comprising amino acid or nucleic acid sequences by combinatorial chemistry. In combinatorial chemistry, a huge number of different sequences is produced by adding each time a single different building unit (amino acid, nucleic acid, or a short amino acid/nucleic acid sequence) to an assembly of newly generated sequences.

The method of the invention can be used so that the newly generated biological molecule, which is being synthesized, is linked to a magnetic particle. Each time a new building block has to be added to the newly synthesized biological molecule the magnetic particle is transferred, by a magnetic device, to a new reaction vessel holding the additional building block. It is preferable to use an array of reaction vessels and a corresponding array of pick-up magnetic devices (multi-pin device) so that a plurality of magnetic particles linked to newly synthesized biological molecules may be transferred at once to a plurality of reaction vessels containing new building blocks to be added. At the end of the synthesis, when all the building blocks have been added, it is possible to disassociate the newly synthesized molecule from the magnetic particle. Alternatively, it is possible to maintain the molecule on the particle for further processing. For example, it is possible to transfer, by a multi-pin device, the magnetic particles linked to the newly synthesized molecules to a membrane for the creation of a peptidic map.

Once the sample is contacted with the magnetic particles'matrix, the biological entities become immobilized on the matrix in a discrete location of the matrix where those magnetic particles which are coupled to the appropriate second member were immobilized. The particles from a specific discrete location in the matrix may then be easily separated from the rest of the matrix and obtained separately. Thus, if the location of a specific species of biological entities in the matrix is known, (e.g. after appropriately staining the magnetic particles'matrix by means well known in the art, such as by enzymatic reactions, immuno-reactions, use of fluorescent or radioactive labels and the like), the magnetic particles having the specific separated species attached thereto can then be easily collected from the matrix, e.g. by using a device having a tapered tip which may be magnetic or non magnetic. The biological entities may then be dissociated from the separated magnetic particles by a variety of means well known in the art: For example, where the pair forming group is antibody/antigen by lowering the pH; or where the pair forming group is two complementary strands of oligonucleotides by raising the temperature (annealing).

In accordance with one embodiment of the invention which will be referred to herein at times as "membranal embodiment", the magnetic matrix is formed on a membrane sheet. In accordance with a second embodiment of the invention termed the "gel embodiment", the magnetic particles are embedded in a gel or present on one of its surfaces. In accordance with a third embodiment of the invention termed "the solid substrate" embodiment, the particles are arrayed on a solid substrate which may be a flat magnet or a glass, plastic metal sheet placed on a magnet. In accordance with a fourth embodiment of the invention termed "the wells embodiment" the particles are present in an array of liquid holding wells which are placed on a magnet.

When performing the various embodiments of the invention the contact between the magnetic particles and the biological entities is achieved by immersing the sheet, gel or solid substrate in the sample solution, or by placing a small amount of sample inside each well. When performing the gel embodiment, the transfer of the biological entities to the magnetic particles is carried out after diffusion of the entities through pores in the gel. Such diffusion may aid in the separation process since the gel itself can serve as a sieve which permits diffusion of entities having a specific size and separation according to size is the first step in the separation process. If desired, magnetic particles having different affinities may be present at different depths in the gel in accordance with the molecular weight of the biological entities to be separated, for example, those magnetic particles capable of binding high molecular weight entities are present on the outer surface of the gel and those capable of binding low molecular weight particles deeper inside the gel.

When performing the membranal embodiment of the present invention and the "solid substrate embodiment" the entities are transferred through the solution directly into the magnetic particles'matrix present on the membrane or on the solid substrate.

The membranal embodiment, the gel embodiment and the solid substrate embodiments may be performed where the substrate is present in a flat form or alternatively where the substrate is formed as a tube so that the magnetic matrix is present on the surfaces of the tube. Such a tube may be formed by a warping membrane sheet to form a hollow tube which is placed inside a column in the membranal embodiment of the invention, or by forming a gel substrate in a hollow cylindrical shape, preferably also placed inside a column. The solid substrate embodiments may also include the possibility of an immobilized matrix of magnetic particles placed on the inner surface of a tube made from glass, iron or an inert plastic material. The matrix may be immobilized via a magnet or magnets attached to the outer surface of the tube. In any of the above descriptions the tube can be made in a column formation or the like. After the sample solution is passed through the tube, the substrate (for example the sheet or gel) can be cut open and the magnetic particles carrying specific biological entities obtained or detected from discrete locations on the substrate as explained above.

The matrix of magnetic particles may be tailored to have various forms as desired. The magnetic particles in the matrix may have an affinity to one species of biological entities, or the magnetic particles may have an affinity to several species of biological entities wherein all magnetic particles having the same affinity (rendered by the species of the second member coupled thereto) are localized in the same discrete location so that each discrete location may be separately detected or obtained.

The present invention further provides methods for the preparation of the matrix of magnetic particles either on a sheet or a solid substrate as an integral part of the gel, or in an array of liquid-holding wells placed on a magnet.

A matrix of magnetic particles on a sheet (or membrane) in accordance with the membranal embodiment of the invention may be formed by manually or automatically applying a solution containing magnetic particles to a sheet, as in printing ink on paper or by a printer inject machine, by a multi-pin device dipped in a magnetic particles solution or by spraying a preparation comprising the magnetic particles on to the sheet.

The magnetic particles' matrix may be formed in accordance with the "solid substrate" embodiment of the invention by immobilizing magnetic particles on a rigid substrate such as a glass slide with a planar magnet attached on its other side or directly on a flat magnet. When using a solid substrate, it is preferred to place on the magnetic matrix a fine net, e.g. made of tin-coated iron, which secures the attachment of the particles to the solid substrate, and eliminates lateral movement of particles from distant regions towards the collecting device, which may occasionally occur where the attachment of the particles to the substrate is not strong.

Alternatively the magnetic particles can be immobilized in slots or small holes on the solid substrate (such as a glass plate) with a strong planar magnet attached on the other side of the substrate under the slots or holes. The particles may be held by the solid substrate simply by magnetic force (of the substrate itself or of a flat magnet placed behind the substrate) or with the aid of an adhering substance such as a suitable glue. The adherence substance may be the complex biotin and nitro-streptavidin which form together a strong complex (one of the pair linked to the magnetic particle and the other to the solid substrate). The use of such a complex as an adhering substance has the advantage of dissociation under relatively mild conditions, thus enabling easy retrieval of the particles from the solid substrate (Morag et al, *Anal Biochem.* 243:257-263 (1996)).

In order to form a gel for use in the gel embodiment of the invention, the matrix may first be formed on a sheet, on a rigid substrate or directly on a magnetic plate in a similar manner as described above and then a molten gel is poured on the sheet, rigid substrate or magnetic plate and allowed to harden, whereby the magnetic particles' matrix forms one of the external surfaces of the gel. The matrix of magnetic particles can also be formed in the gel by mixing the magnetic particles with the molten gel and prior to hardening of the gel causing the particles to move to one of the surfaces, e.g. by the use of a magnet or the several discrete locations in the surfaces or several magnets arranged in a desired pattern.

The matrix can also be formed as dots or lines in the gel by injecting magnetic particles into the molten gel prior to hardening of the gel causing the particles to move to one of the surfaces, e.g. by the use of a magnet or several magnets arranged in a desired pattern. Alternatively, the magnetic particles can be applied to appropriate slots in the gel, preferably by applying a hot preparation of magnetic particles to the gel.

Sheets for use in the membranal embodiment of the invention and gels for use in the gel embodiment of the invention, solid substrates with magnetic forces and a liquid-holding well arrangement placed on a magnet, also form an aspect of the present invention.

Another aspect of the invention are kits for carrying out the above method. The kits can comprise the membrane, gel, solid substrate or liquid-holding well arrangement for holding the magnetic particles' matrix; flat magnet or matrix of magnets and a device for collecting magnetic particles with a tapered tip, agents capable of processing the gel, membrane, liquid in the well or solid substrate to produce a detectable label such as fluorescent, radioactive antibodies or enzymes required for carrying out a color reaction and the like; rinsing buffers and agents for separating the biological entities from the magnetic particles, etc.

The method of the present invention has several advantages as compared to prior art methods:

(1) The biological entities separated from a sample solution in accordance with the invention can be easily recovered by collecting the magnetic particles and optionally dissociating the entities therefrom. The dissociation can be performed by transferring the magnetic particles into small volumes of suitable solutions with a very small loss of the biological entities, or alternatively by arranging those magnetic particles which bind the biological entities from the previous matrix to form a new matrix, for example, for sequencing by hybridization purposes.

(2) Where the separation of the entities is performed as part of an analysis, only entities of interest remain attached to the matrix of magnetic particles which is then further analyzed, which feature considerably lowers the background signals which can otherwise be created by other entities. Accordingly, analysis performed in accordance with the present invention yields a more accurate result, which can more easily be interpreted.

(3) The method of the present invention allows multiple probing of the biological entities separated from the sample. In accordance with prior art methods, the binding of the separated biological entities to the substrate in which the probing was performed, e.g. a nitrocellulose sheet, was weak and consequently it was generally not possible to carry out multiple probing since after each probing it was necessary to wash the matrix which brought about a considerable loss of the tested biological entities from the matrix. In accordance with the present invention, owing to the fact that the biological entities of interest are bound with a high affinity to the magnetic particles in the matrix which are in turn immobilized, washing of the magnetic matrix will result in only a very minimal loss of the entities, whereby multiple washes and hence multiple probing becomes possible.

(4) In accordance with the method of the invention, each species of biological entities may be easily separated from the rest and may then undergo separate treatments, e.g. different types of probing, etc.

(5) The method of the invention enables simultaneous different detections of several species of biological entities of the same sample solution. For example, it is possible to detect simultaneously all different species of bacteria present in one sample.

(6) The method of the invention enables to carry out the detection of a single species of biological entities simultaneously on a plurality of sample solutions. For example, it is possible to detect simultaneously presence of one bacteria in many samples obtained from different patients.

The present invention will now be further illustrated and exemplified with reference to some non-limiting drawings and examples.

GENERAL DESCRIPTION OF THE INVENTION

The biological entities to be separated in accordance with the invention may be proteins, glycoproteins, peptides, DNA entities and RNA entities both from natural source or synthetically produced, such as genetically engineered peptides or fragments of recombinant DNA. The biological entities can comprise a biotin moiety and in such a case the magnetic particles are coupled to streptavidin. The biological molecules may also be whole cells, bacteria, virons, plasmids or various cellular organals such mitochondria, nuclei and the like.

The magnetic particles may be particles having a wide range of diameters, particles having diameters in the range of 100–1500 nm being preferred. Relatively larger particles are preferred when using a solid substrate, so that enough magnetic force is applied to them to ensure the immobilization of the particles. The magnetic particles comprise a core made of a magnetic substance such as ferrous oxide and optionally having a coating which confer the particles binding specificity. Suitable particles are, for example, BioMag™ (Advanced Magnetics Inc., Cambridge, Mass., USA). Various types of BioMag™ particles are available having each an affinity to a different specific species of biological entities.

The magnetic particles may have a uniform distribution pattern in the matrix made from dots or may be non-uniformly distributed in a pattern of strips of particles and the like. The strips may be, for example vertical or horizontal or diagonal. Typically, each strip made of dots of magnetic particles having affinity to a specific species of entities.

It is possible also to have several strips of varying specificities arranged in an alternating pattern along the substrate which may be a membrane, a gel or a rigid substance.

Figure 1:
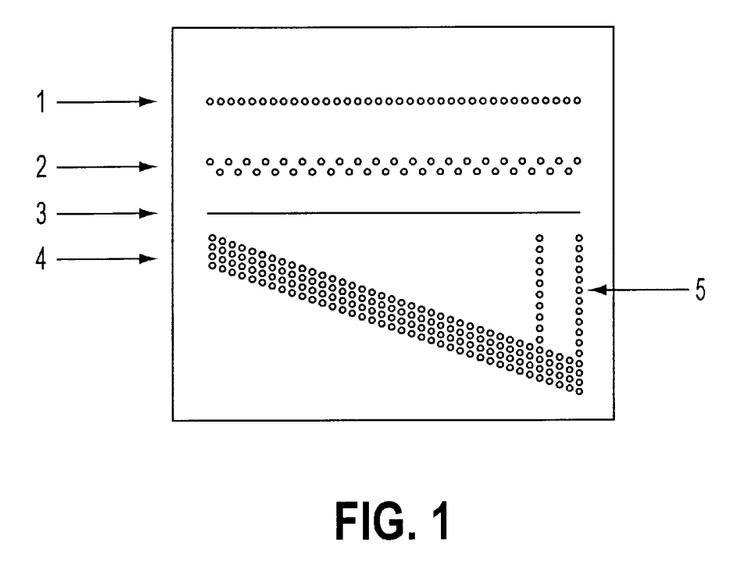
FIG. 1 shows a filter sheet in accordance with the membranal embodiment of the invention having a matrix of magnetic particles.

An example of a matrix of magnetic beads is shown in FIG. 1, wherein 1 is a horizontal strip of dots of magnetic particles coupled to a second member of a pair forming group having an affinity to a first species of biological entities; 2 is a strip of two lines of dots of magnetic particles coupled to second members having an affinity to a second species of biological entities; 3 is a continuous line composed of magnetic particles coupled to second members having an affinity to a third species of biological entities; and 4 and 5 are diagonal and vertical dots coupled to second members having a affinity to fourth and fifth species of biological entities, respectively. The magnetic particles are formed in different patterns in order to ease the distinguishment between them. The sheet is immersed in the sample solution in order to enable contact between the biological entities and the magnetic beads.

Figure 2:
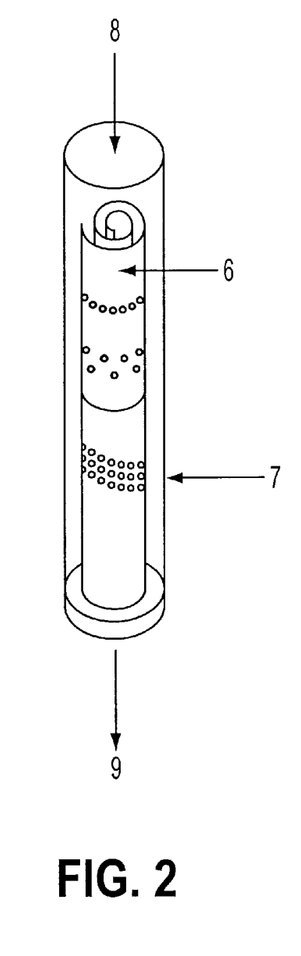
FIG. 2 shows the filter sheet of FIG. 1 wrapped to form a tube for producing a separation column.

Alternatively, the sheet may be formed into a tube 6 as shown in FIG. 2 and placed within a column 7 having an in flow 8 and an out flow 9. The sample solution is then passed through column 7 and biological entities bind to the sheet with the binding affinity of the second members coupled to the magnetic particles.

Biological entities from the sample solution are transferred to the matrix of magnetic particles in the membranal embodiment or the solid substrate embodiment by contacting the membrane or solid substrate with the sample solution. In the gel embodiment the entities are transferred from the sample solution to the magnetic particles via diff fusion through pores in the gel contacting the sample solution, and in such a case the gel should be immersed in the sample solution. The biological entities are transferred to the magnetic particles in the well embodiment simply by placing a small amount of the sample in each liquid-holding well.

Biological entities which were separated from the sample solution and which are bound to the magnetic particles can be subjected to various analytical probings such as: binding to monoclonal antibodies linked to detectable markers; reactions with various enzymes; contact with labeled complementary DNA fragments; staining with specific dyes such as ethidium bromide and the like, as the case may be. Some dyes may at times be undetectable on the particles themselves due to their dark color. In order to facilitate identification of a dot on the matrix in the membranal embodiment, particularly where the substrate holding the magnetic particles is a sheet such as paper or nitrocellulose, it is useful to leave portions of the sheet free of magnetic particles, for example, by forming a dot of magnetic particles having small free areas therein between. Staining, which is visible on said free areas, will indicate the identity of the biological entities that were affinity bound to the magnetic particles in the dot present adjacent to said free areas.

A. Purifying the separated biological entities

Figure 5:
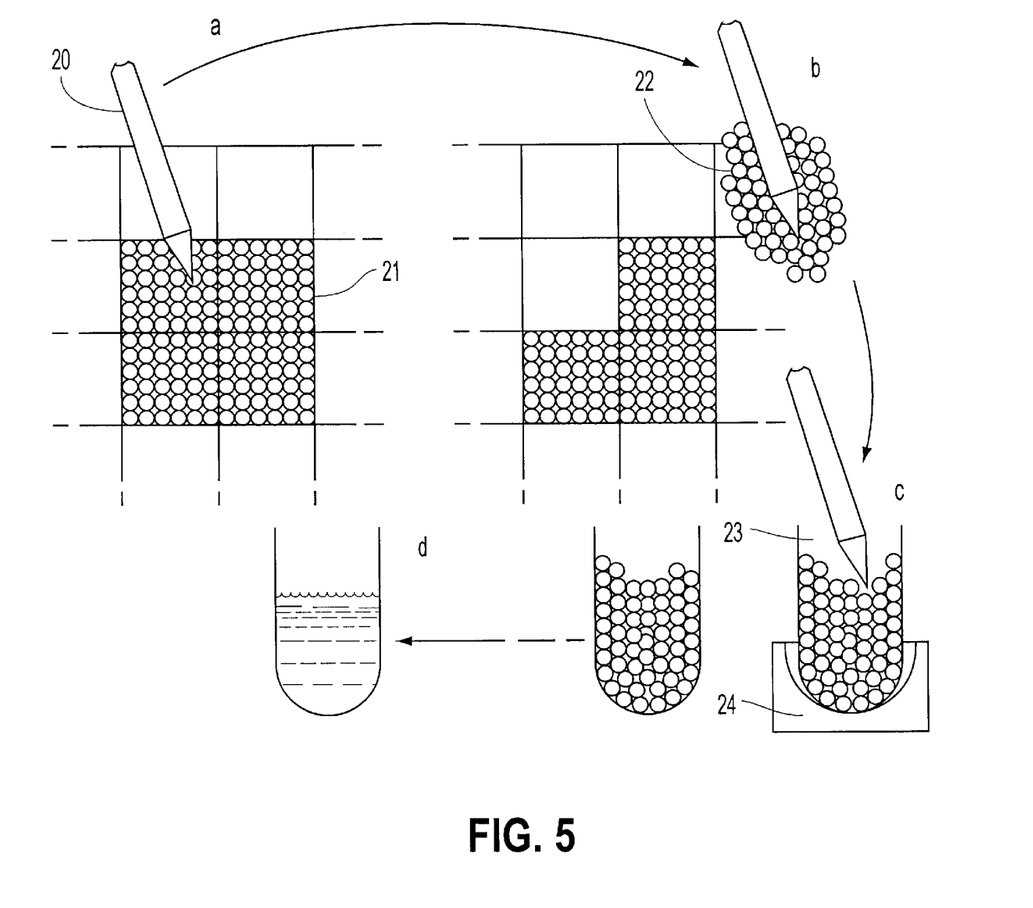
FIG. 5 shows a method for isolating magnetic particles.

Purifying the separated biological entities may be carried out by transferring the magnetic particles to small vessels such as a well of a microwell plate. In order to ensure that the particles are not lost, a magnet can be placed below the vessel in which the obtained particles are placed (FIG. 5(c) element 24 as will be explained hereinbelow). The bound entities can be dissociated from the particles by any means known per se depending on the nature of the specific binding between the particles and the biological entities. For example, where the magnetic particles are coupled to an antibody and the biological entity is an antigen, separation may be carried out by lowering the pH. The free magnetic particles can be removed by the use of a magnet, and, if desired, can be washed and recycled for further usage. It is sometimes advantageous to keep the separated biological entities bound to the magnetic particle, such as, for example, where the separated entity is a DNA entity to be subjected to PCR treatment, in which case it is preferable to have one strand immobilized (Hultman, T., et al., *Bio Techniques,* 10(1):84–93, (1991)).

Magnetic particles bound to separated biological entities may be obtained and then dotted on a membrane sheet to form a new matrix of magnetic particles composed only of those magnetic particles which bind the biological entities. Such a matrix can be smaller than the starting matrix and hence more economical in terms of probe quantity needed for detection. A second type of sample can be added and again, only those magnets which bind to the second biological entity are obtained in order to form a second, third, etc. high density magnetic matrix. Such formation of new matrices from magnetic particles obtained in the previous step is suitable for multiple probing, such as for sequencing by hybridization and detection of probes via peptide libraries. This technique eliminates the need for multiple washing of the filters and the stripping off of the probes from the filters.

Figure 4:
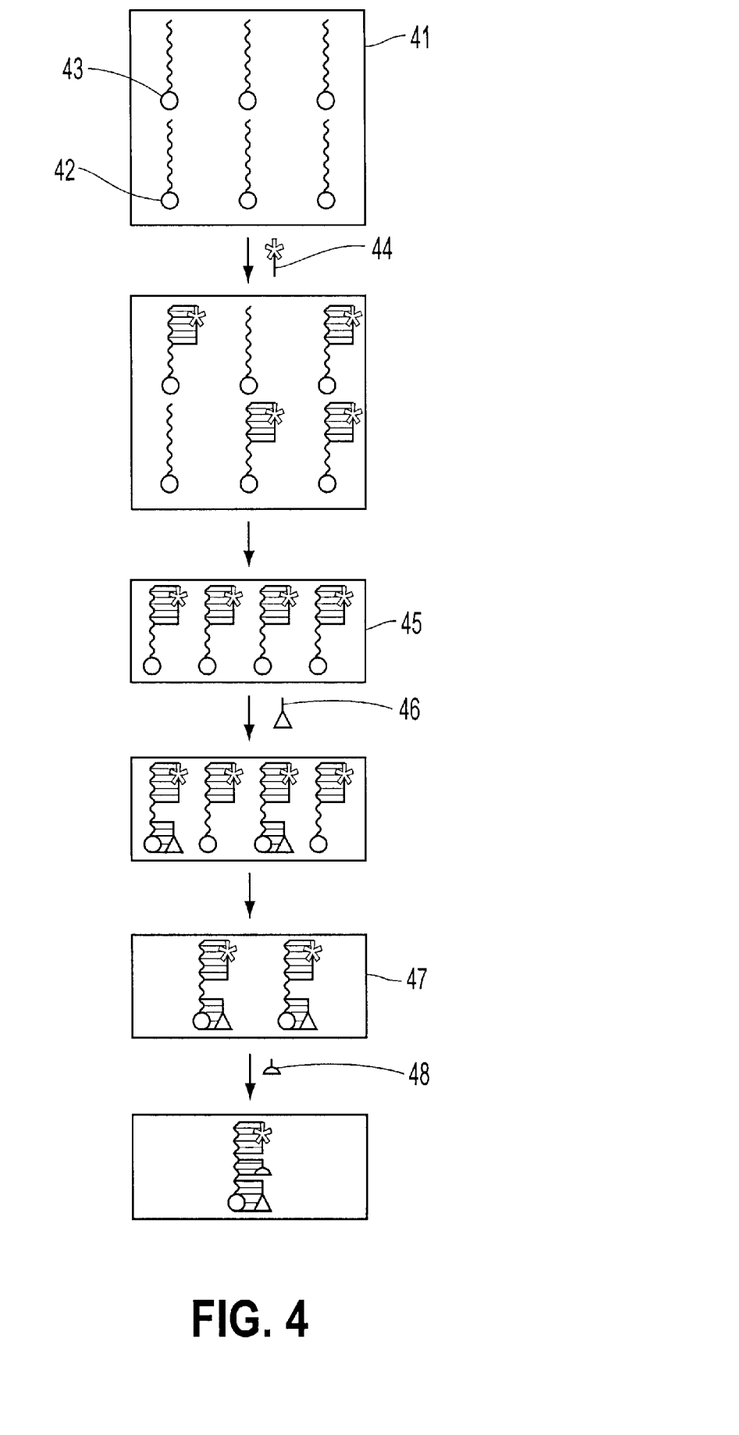
FIG. 4 shows the utilization of the method of the invention for sequencing by hybridization.

An example of sequencing by hybridization is shown in FIG. 4. 41 shows a first matrix of magnetic particles 42, each attached to a nucleic acid sequence 43. In reality of course each location in the matrix is made of a plurality of magnetic particles coupled to nucleic acid sequences. Probe 44, which is a short oligonucleotide having a known sequence and bearing a first detectable label (*) is brought into contact with the matrix 41 and allowed to hybridize with the sequence 43. Only those nucleic acid sequences which hybridized to labeled probe 44 are collected and are arranged to form a new matrix 45 composed only of nucleic acid sequences which hybridized to probe 44.

A new and known probe 46 labeled with a second detectable label (Δ) is then added to matrix 45 and only those particles having sequences, which hybridized to probe 46 are collected and placed on new matrix 47.

A third known probe 48 having a third detectable probe (Δ) is contacted with matrix 47 and only these particles which hybridize with sequence 48 are collected. Since each time only the sequences which hybridize with the new sequence are collected, finally there remain only magnetic particles attached to sequences which hybridized to all the small known probe sequences used, and by this it is also possible to determine the sequence of the nucleic acids immobilized on the magnetic particles. In practice, each new matrix 45, 7, etc. is smaller than the previous matrix since it contains less sequences so that it may occupy a smaller area than the previous matrix.

The collecting of the magnetic particles may be carried out for example by a tapered magnetic collecting device (FIG. 5(a), 5(b) and 5(c)see below). Such a collecting device may suitably comprise an electromagnet allowing the attachment of the particles upon application of an electric field and release of the particles upon termination of the electric field. It should be noted that the collecting device may be composed of a single collecting member, or may be composed of a plurality of collecting members, for example, a plurality of metal pins which become magnetized by attachment to a magnet and de-magnetized by detachment from a magnet.

The collection of the particles may be automated, e.g. by the use of a magnetic collecting device which position is controlled by a servo x-y machine.

If the magnetic particles are adsorbed on a sheet, they may be collected by controllably applying a suitable solvent such as water or acetone to a chosen location of the matrix so as to loosen the adsorbance of the particles to the sheet without completely disconnecting them therefrom and then collecting them by a tapered magnetic device as described above. Alternatively, the magnetic particles released from the sheet by the solvent may be collected by using non-magnetic tapered collecting devices such as capillary, a pipette, a glass pin and the like.

The membrane sheet can be placed on a planar magnet or a matrix of many magnets present on a planar surface in order to immobilize the magnetic particles and then the sheet can be dissolved by a suitable solvent. For example a nitrocellulose sheet can be dissolved by acetone. After controlled dissolvement of the membrane sheet the whole magnetic matrix still remains immobilized to the planar magnet and can easily be obtained therefrom.

The same procedure can be applied for the gel embodiment, in which case an agarose gel is placed on a planar magnet or planar matrices of many magnets followed by controlled dissolving of the gel with a suitable solvent such as sodium iodide. The whole magnetic matrix in such a case also becomes immobilized to the planar magnet.

Figure 3:
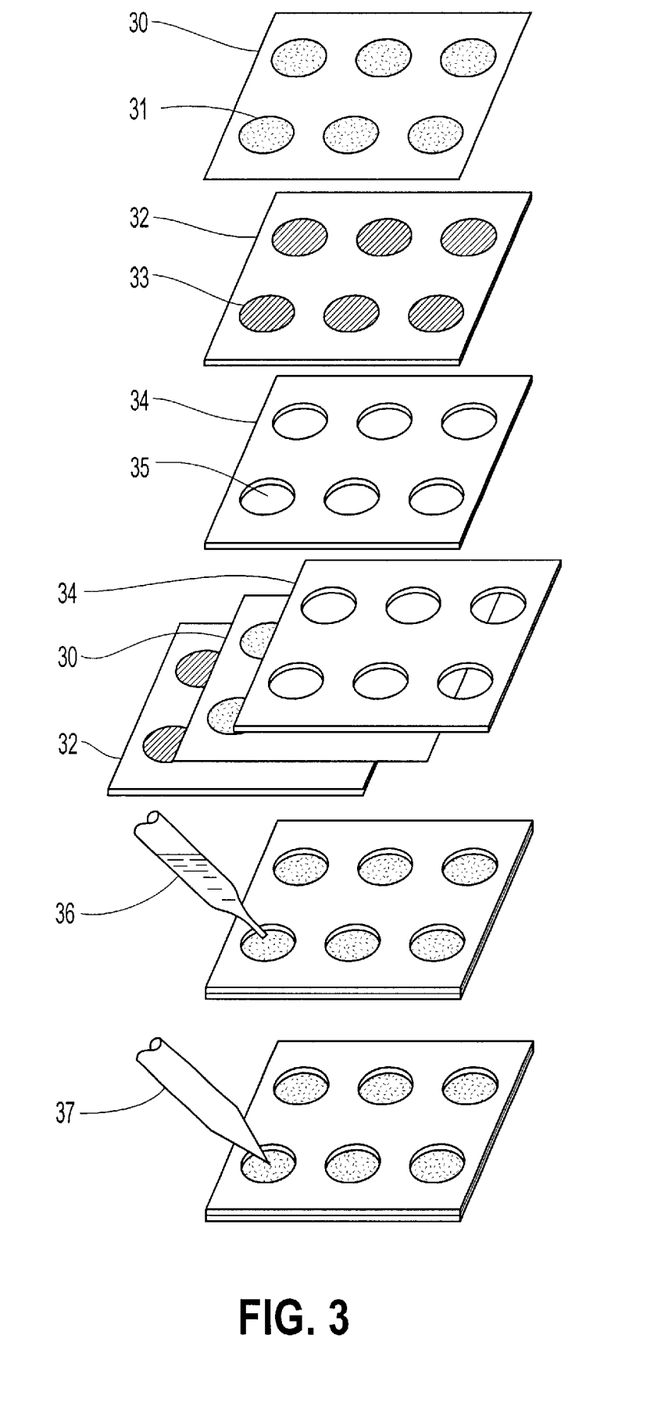
FIG. 3 shows steps in purifying the magnetic parties from a discrete location in the matrix.

FIG. 3 shows the separation of magnetic particles from a specific location of a nitrocellulose sheet. Although FIG. 3 refers to separation from a sheet the same essential steps are applicable also for separation from a gel. The figure shows a nitrocellulose sheet 30 comprising a matrix of dots 31 each composed of a plurality of magnetic particles; a matrix 32 of round magnets 33 formed on a plastic board and corresponding in pattern to matrix 30; and a rubber board 34 having holes 35 in a pattern corresponding to matrix 30. The three flat surfaces are arranged as follows (from bottom to top) matrix of magnets 32, matrix of magnetic particles 30 and rubber board 34 and are attached together. Such an arrangement ensures that each dot of magnetic particles on the nitrocellulose sheet is placed on a round magnet, and that the ridges of each hole 35 create a small well around each dot 31. Acetone is applied by pipette 36 to a specific hole, locally dissolving the nitrocellulose sheet only inside the boundaries of a specific hole. Board 34 ensures that the solvent does to leak to other regions of the sheet The particles released by the sheet are then attracted to the magnet 32 present beneath. A tapered magnet 37 is then used to collect the magnetic particles released from the sheet.

When performing the membranal embodiment and particularly when performing the invention with a matrix formed on a solid substrate (where the substrate holding the magnetic particles' matrix only weakly holds the particles), it is preferred to place a net on the matrix (FIGS. 5(a, and 5(b)). Such a net ensures a localized collection of particles as it avoids lateral movement of distant particles during the collection process. Where the net is made of a ferromagnetic substance, there is a local magnetic field formed inside the holes of the net which holds the particles inside the holes relatively firmly.

FIG. 5 shows the isolation of particles from a specific hole in the net from the matrix. As shown in FIGS. 5(a) and 5(b), a tapered magnetic device 20 collects magnetic particles from a specific hole 21 in the net the particles 22 attached to device 20 as shown in FIG. 5(b) are then transferred into a small vessel 23 placed on top of a magnet 24. By turning off the electromagnet of device 20, the particles 22 collect inside vessel 23 as shown in FIG. 5(c) and then the biological entities can be recovered from the magnetic particles as shown in FIG. 5(d). ps B. Preparation of the matrix of magnetic particles 1. The membranal embodiment The matrix of magnetic particles can be formed by adsorption or absorption of the particles to a suitable sheet such as a filter paper, nitrocellulose sheet, pergameneous material sheet, cellulose acetate xerographic paper or polycarbonate membrane. It is at times preferable to use sheets that can be dissolved by a suitable solvent in order to facilitate the collection of the particles after the binding step, cellulose acetate sheet being especially preferred for such a purpose.

Alternatively, it is possible to use at times sheets which are not dissolved by solvents, for example xerographic paper which strongly absorbs or adsorbs the magnetic particles. Xerographic paper generally has small pores and the particles which enter such pores strongly stick thereto and cannot easily be removed. Matrices formed on such strongly absorbing sheets are used for detection purposes.

The magnetic particles can be applied to the sheet manually or using an automated printer such as inject printers. The printer can use simultaneously several "pens" each containing a solution of particles having a different binding affinity. The magnetic particles can also be sprayed on the sheet.

2. The gel embodiment

The gel to be used in accordance with the present invention may for example be agarose gel. The matrix of magnetic particles may, in accordance with the gel embodiment, be included as a layer in the gel, close to one of its external surfaces.

When carrying out this embodiment, contacting the particles with the biological entities in the sample solution may suitably be performed by gently heating the surface near the matrix layer of the gel while drawing the particles towards a magnet at the surface.

As an alternative to melting the gel by heat, the gel may also be dissolved by the use of chaotropic agents such as solutions with high concentrations of potassium iodine, sodium perchlorate or sodium iodine. Even where chaotropic agents are used it is preferred that during dissolution the gel be gently heated to about 45° C. Another possibility is a digestion of the gel, for example by GELASE™ (Epicentere Technologies, USA) which digests the carbohydrate backbone agarose gel.

C. Preparation of the kit of the Invention

The kit of the invention may comprise a gel containing an immobilized matrix of magnetic particles for use in the gel embodiment, a sheet with an immobilized matrix of magnetic particles for the membranal embodiment and rigid substrate with a stock of suitable magnetic particles, the latter two optionally accompanied with a net to be placed on the matrix. In addition, the kit may comprise a flat magnet, or a matrix of magnets on a flat surface, which is at times suitably lightly colored or coated with an inert substance having a light color so as to provide a contrast for the particles which have a dark color. In addition, the kit may comprise various reagents such as solvents for freeing the particles from the matrix in which they are contained or agents for use in the separation of the biological entities from the particles, chaotropic agents for dissolving the gel, enzymes for digesting the gel, various reagents necessary for producing a detectable label such as labeled antibodies, devices for collecting the particles which may comprise a single collecting member or a plurality of collecting members, microwells with associated magnets below their bottoms, etc.

DETAILED DESCRIPTION OF SPECIFIC EMBODIMENTS

EXAMPLES

Example I

A. Construction of the magnetic matrix

Eight flat square fine tincoated magnets, 20 mm each side and 4 mm thick (VACODYM198 370 HR P/N 66750490, Vacuumschmelze GmbH, Germany) were attached in pairs to give 4 (40 mm×20) mm rectangles. Each of the 4 rectangles were separated from each other by 40 mm×20 mm×2 mm rubber sheets, to form alternating layers of magnets and rubber. This construction forms a box which narrow side has 4 strips of magnets 40 mm long and 4 mm wide, separated by strips of rubber 40 mm long and 2 mm thick and will be referred to hereinafter as the "stripped magnet", or a flat magnet.

The above box can also be constructed without use of the rubber strips so its side has a dimension of 40×16 mm or 20×32 mm, which construct will be referred to hereinafter as the "uniform magnet".

B. Preparing a magnetic particle matrix integrated in agarose

A silicon rubber rectangular frame 1 mm thick, 7×7 cm outer dimension and 5×5 cm inner casting space was attached, via silicon grease (Silicaid, Aidchim Ltd., Israel) to a 7×7 cm clean glass plate. The glass plate was placed on the stripped magnet, prepared as described in A above and heated with a hair dryer. 200 $\mu$l from 1 $\mu$m diameter superparamagnetic ferrous oxide particles which were coated with a functional affinity group (Advanced Magnetics, Inc., USA) were drawn from a 50 mg/ml stock solution and were injected to 3 ml of a 2% aqueous solution of low melting point agarose (A-9414, Sigma Chemical Co., USA) at a temperature of 45° C. and mixed for 1 minute by a vortex. The agarose was poured into the casting space and then covered with a 7×7 cm hot glass plate. After a few minutes at 35° C. the gel was allowed to cool and was left at room temperature for at least one hour. During this time the magnetic particles were drawn to the stripped magnet and a stripped matrix of magnetic particles at the bottom layer of the gel was then obtained. The same procedure was repeated with the uniform magnet, whereby a uniformed matrix of magnetic particles was obtained.

If extra support to the gel is desired, an inert polypropylene support net 100 $\mu$m thick with a pore diameter of 200 $\mu$m may be placed in the casting space prior to pouring of the gel.

Alternatively, the agarose gel was prepared as above without adding the magnetic beads to the molten gel and was allowed to cool and harden at room temperature.

The gel was left to cool and harden on a glass or a plastic plate having a specific pattern of protrusion, which consequently cause a corresponding pattern of depression in the cooled gel. Into the pattern of depression 1 $\mu$m diameter superparamagnetic beads ferrous oxide particles coated with a functional affinity group were injected. It was possible to use different affinity particles at predetermined locations in the gel. The injected particles were at a temperature near the melting point of the gel in order to effect local dissolvement of the gel at the location of application so as to bring to immobilization of the particles in the gel.

C. Isolation of magnetic particles

An agarose gel prepared as described above, was placed on a flat magnet of 40×40 mm in size which was constructed with a uniform magnet obtained by placing 4 magnets one beside the other on a flat 7×7 cm tin-coated iron plate 0.3 mm thick which was used for extra support. The gel was placed on the magnet so that the layer of magnetic particles was facing downwards near the magnet and its ends were carefully cut, to give a gel size of 40×40 mm. A rectangular rubber frame 2 mm thick, 5×5 cm outer dimension and 3×3 cm inner space was placed on the gel and held by the magnetic force of four 0.5×5.0 cm iron sheets which were placed on it. 2 ml of saturated NaI aqueous solution at 38° C. was poured into the inner space of the rubber frame. After 5 minutes all the gel was dissolved and the solution with the dissolved gel was then poured away by tilting the plate. The stripped or uniform patterns of the magnetic particles were transferred to the uniform magnet with no substantial change. Remainders of wet agarose were washed away and the beads were collected with the aid of a tapered magnetic device.

Example II

Preparation of a matrix of magnetic particles as an integral part of the gel

A solution of magnetic particles (EMG 705 Water Base Ferrofluid Ltd., Israel) was manually applied on to the surface of pergameneous paper with the aid of the tip of a glass Pasteur pipette in a pattern of diagonal strips, and left to dry for 1 hr.

The paper was then glued to a glass plate via contact glue or a double face adhesive tape. A silicon rubber rectangular frame, 1 mm thick, 7×7 cm outer dimension and 5×5 cm inner casting space was placed on the glued paper and attached by 4 clips. The glass plate was placed on a gel casting table equilibrated to a temperature of 35° C. A polypropylene support net, 100 $\mu$m thick, 200 $\mu$m pore diameter was placed into the casting space prior to pouring the gel. 3 ml of 2% aqueous solution of agarose low-electroendosmosis (05071, Fluka, Switzerland) in a temperature of 60° C. was poured into the casting space. The gel was covered with a glass plate and left to solidify at room temperature for at least one hour. The resulting gel contained on its surface the replica of the magnetic particles originally formed on the sheet Example III Collecting of magnetic particles from a specific location in a matrix Four magnets as described above were placed on a 7×7×0.3 cm tin-coated iron plate in two pairs and separated from one another by a gap of 3 cm. The tin-coated iron plate was placed on the magnets and a tin-coated iron net having holes in the size of 1 mm was placed on the iron plate and held by the magnetic force of the two pairs of magnets. 1 gr iron powder, 50–150 $\mu$m in particle size, was placed on the net and gently spread in the net area above the 3 cm gap between the magnets. The net and magnetic force held the particles so tightly that a wet filter paper placed on the net and pressed by a second tin-coated iron plate for 10 min. did not remove any of the particles.

A tapered electromagnet was used to collect the particles from the net. The net enables the collection of particles from each hole of 1 mm in size separately, with no lateral movement of particles from the other holes (see FIG. 5(a) and 5(b)). The tip of the tapered electromagnet was placed inside a well in a microtiter plate fixed on an adapter with a built-in matrix of permanent magnets (BioMag™ Separator 4101S, Advanced Magnetics, Inc., USA). Shutting off the current of the electromagnet caused the transfer of the particles from the electromagnet's tip to the well.

Example IV

A. Formation of a matrix of magnetic particles on a sheet (i) A 5×5 cm sheet of cellulose acetate (S & S, OE67) 0.45 $\mu$m porosity was moistened with distilled water and then attached by adhesion to a 10×10×0.1 cm glass plate. Excess water was discarded and a nylon net with 200 $\mu$m holes was attached to the sheet to eliminate movement of the particles. The glass plate was laid on the stripped magnet prepared as in A above, and attached to the matrix by an adhesive tape for extra support.

50 $\mu$l of an aqueous suspension of ferrous oxide particles described above in Example I were diluted with 10 ml distilled water and the diluted suspension was sprayed on the nylon net attached to the sheet, from a distance of 3–5 cm, while holding the combined sheet and glass plate at an angle of 45°–90°. The magnetic particles became attached to the sheet at a striped pattern corresponding to that of the magnet. The sheet was left to dry and drying was enhanced by placing blotting paper or filter paper at the sides of the cellulose acetate sheet. The nylon net was then removed, and the matrix of magnetic particles retained the striped pattern, but each stripe was formed of dots as a result of the nylon net.

The same procedure was repeated with nitrocellulose sheets (S & S, BA85).

(ii) The solution of ferrous oxide particles described above was drawn into a pipette tip (100 $\mu$m tip) by a Nichiryo Model 5000 Pipetor 10–50 $\mu$l (Japan) and with the aid of the tip strips at a desired pattern were applied on a cellulose acetate sheet. By using a volume of 20 $\mu$l line of 4 cm long and 0.5 mm wide and 15 dots of approximately 1 mm diameter each could be drawn.

B. Isolation of magnetic particles

A filter sheet prepared as described above (A(i)) was attached to a flat magnet, with the matrix of magnetic particles facing towards the magnet. A rubber frame having an inner space of 3×3×0.2 cm was attached to the sheet and 2 ml acetone 100% was added into the inner space. After 5 min. the acetone was discarded and replaced by 2 ml fresh acetone and the procedure was repeated 5 times. The filter sheet was digested while the particles remained on the flat magnet in their original pattern and could be collected with the aid of a tapered electromagnetic device. Magnetic particles were bound to the tip of the device because of the very high local magnetic field exerted upon them. The tip of the electromagnetic collecting device was then placed inside a well in microtiter plate fixed on an adaptor with a built-in matrix of permanent magnets, and the current activating the electromagnet was shut off and consequently the particles were pulled from the tip of the collecting device into the well.

Example V

Point isolation of magnetic particles from a sheet

A filter sheet prepared as described above in Example IV was laid on a glass plate, with the matrix of magnetic particles facing upwards. The matrix was gently touched with a capillary glass tube containing 5 $\mu$l acetone. The filter sheet was locally dissolved by the acetone present in the capillary and magnetic particles from the touched point were immediately sucked into the tube via capillary force, and thus collected. The particles were ejected from the capillary into a suitable vessel, such as a well by application of pressure. The vessel was placed on a magnet in order to facilitate magnetic separation of the particles from the solution.

Example VI

A. Preparing a magnetic particle matrix via injection into a gel

A silicon rubber rectangular frame 1 mm thick, 7×7 cm outer dimension and 5×5 cm inner casting space was attached, via silicon grease to a 7×7 cm clean glass plate. The glass plate was placed on the stripped magnet, prepared as described in Example I(A) and heated with a hair dryer. 3 ml of a 2% aqueous solution of low melting point agarose as disclosed in Example I at a temperature of 45° C. was poured into the casting space. 10 $\mu$l of 1 $\mu$m diameter superparamagnetic ferrous oxide particles which were coated with a functional affinity group (as in Example I) were injected via a manual pipetor into the gel. Injection was done with the pipetor tip gently touching the surface of the gel and moving the tip along a magnetic strip. The particles were immediately drawn to the stripped magnet and a fine focused strip of magnetic particles appeared at the bottom layer of the gel. The gel was allowed to cool at room temperature for at least one hour.

B. Isolation of magnetic particles

An agarose gel prepared as described above, was placed on the stripped magnet (described in A above). The gel was placed on the magnet so that the layer of magnetic particles was facing upwards, the strip of magnetic particles located above and parallel the magnet strip. 10 $\mu$l of saturated NaI aqueous solution was injected into a frame slot in the gel's upper surface, above and along the strip of magnetic particles. After 5 min. the strip of magnetic particles was located in a deeper layer of the gel.

Example VII

Collecting of magnetic particles from a specific location in a matrix

A 7×7 cm 2 mm thick glass plate, with 8 parallel slots each 4 cm in length and 0.3 mm deep was placed on the stripped magnet (as described before) so that at least two slots were above and along the stripped magnet. Iron powder 50–150 $\mu$m in particle size, was placed on the glass plate and gently spread over the slots so that the particles immobilized in the slots.

A tapered electromagnet was used to collect the particles from specific points in the matrix. There was no lateral movement of particles adjacent to those picked up, so that only particles which actually were touched by the tapered electromagnet were obtained.

The tip of the tapered electromagnet was placed inside a well in a microtiter plate fixed on an adapter with a built-in matrix of permanent magnets (as in Example III). Shutting off the current of the electromagnet caused the transfer of the particles from the tip to the well.

Example VIII

Preparing a magnetic matrix via injection of magnetic particles to a solid gel

A silicon rubber rectangular frame 5 mm thick, 7×7 cm outer dimension and 5×5 cm inner casting space was attached, via silicon grease to a 7×7 cm clean plastic plate. The plastic plate comprised protrusions in the form of three parallel lines 4 cm each, 1 millimeter wide raise up 3 millimeters from the plastic surface.

13 ml of a 2% aqueous solution of low melting point agarose as in Example I at a temperature of 45° C. were poured into the casting space. After half an hour at room temperature for cooling purposes the solid gel was taken out of the frame.

The gel surface that was in contact with the protrusion in the plastic plate featured three corresponding parallel slots 4 cm each. 10 $\mu$l hot magnetic particles (as in Example VI) were injected via a micropipette into each slot. After a few minutes at room temperature the particles were immobilized to the gel.

Example IX

Formation of a magnetic matrix on a filter sheet

A. Manually

A micro glass capillary pipette (CEEBEE-PETS, Volume end to end 2 lambda from CHR. BARDRAM Denmark) filled with 2 $\mu$l suspension of superparamagnetic ferrous oxide particles 1 $\mu$m diameter, was contacted with a 5 cm diameter cellulose acetate sheet (Schleicher & Schuell) ST69 1.2 $\mu$m pore size. 28 magnetic dots were created. When the particles suspension was diluted 1:2 with water, 2 $\mu$l permitted dotting 70 magnetic dots resulting in 28 nano-liters of particles suspension per one magnetic dot.

B. With a multiping device 1.5 $\mu$l from a suspension of BioMag streptavidin magnetic particles as in Example X, were pipetted into each well in a row of 8 wells in a polypropylene, 96-well plate from Nunc (Denmark). A digital multichannel pipette from Finnpipette (Helsinki, Finland), with 8 channels of icro Finntips, was used to deliver a 0.7 $\mu$l volume of the particles suspension from each well in the plate to a cellulose acetate membrane sheet (as in the Manual Example) of 8×12 cm, creating a row of 8 magnetic dots on the membrane.

Using a plate of 96 holes laid above the membrane as a guide for the pipette tips permitted creation of 96 magnetic dots on the membrane. Such a membrane is in the standard 96 format.

Example X

Streptavidin magnetic matrix on a filter sheet

40 $\mu$l of BioMag streptavidin magnetic particles approximately 1 $\mu$m in size from PerSeptive Diagnostics (USA), were washed twice in phosphate buffered saline (pH 7.2). A BioMag™ Separator from Advanced Magnetics (USA) was used to separate magnetically the particles from the buffer in a 500 $\mu$l Ependorf tube. Buffer was pipetted out leaving 40 $\mu$l of washed particles.

A micro glass capillary pipette (CEEBEE-PETS) was used as in Example IX to create one dot of approximately 0.5 $\mu$l on 1×1 cm filter sheet. Dots were blotted on cellulose acetate membrane filters from Schleicher & Schuell (Germany) and on polycarbonate membranes from OSMONICS (USA).

300 $\mu$l of 0.5% Tween 20 were added to each dot, the membranes were left for half an hour at room temperature. After discarding the Tween 20, 2 ml saline solution was added to each dotted membrane in a small petri dish. The membranes were washed via shaking for half an hour at room temperature.

10 $\mu$l of 1:100 diluted Biotin-Peroxidase from SIGMA was added to each magnetic dot, membranes were left for half an hour at room temperature. 2 ml saline was added to each dot membrane in a petri dish and shaken for 5 minutes, washing was done twice. Membranes were put on filter paper to minimize solution content 2 $\mu$l of 4-Chloro-1-Naphthol substrate suitable for use in immunoblotting from SIGMA was added to each magnetic dot. After a few minutes incubation at room temperature blue rings appeared on the membranes around control magnetic dots (without Tween 20) compared to test membranes that were colored inside the magnetic dots.

Example XI
Anti-Human IgG magnetic matrix on a filter sheet

40μl of BioMag Goat anti-Human IgG (Fc Specific) magnetic particles approximately 1μl in size from PerSeptive Diagnostics (USA) were washed twice in phosphate buffered saline (pH 7.2). A BioMag Separator from Advanced Magnetics (USA) was used to separate magnetically the particles from the buffer in a 500 μl Ependorf tube. Buffer was pipetted out leaving 40 μl of washed particles.

A micro glass capillary pipette (CEEBEE-PETS) was used as in Example IX to create one dot of approximately 0.5 μl on 1×1 cm filter sheet. Dots were blotted on cellulose acetate membrane filters from Schleicher & Schuell (Germany) and on polycarbonate membranes from OSMONICS (USA).

300 μl of 0.5% Tween 20 were added to each dot, the membranes were left for half an hour at room temperature. After discarding the Tween 20, 2 ml saline solution was added to each dotted membrane in a small petri dish. The membranes were washed via shaking for half an hour at room temperature.

1–10 μl of diluted human serum is applied to each magnetic dot, and incubated for 60 minutes at 37° C. The membranes were washed with 2 ml saline each while shaking at room temperature for half an hour.

10 μl of diluted affinty isolated antibody to Human IgG (Fab Specific) labeled with peroxidase from SIGMA (ISA) was added to each magnetic dot, membranes were left for half an hour at room temperature (or incubated for 30 at 37° C). 2 ml saline was added to each dot membrane in a petri dish and shaken for 5 minutes, washing was done twice. Membranes were put on filter papers to minimize solution content.

2 μl of 4-Chloro-1-Naphthol substrate suitable for use in immunoblotting from SIGMA was added to each magnetic dot. After a few minutes incubation at room temperature blue rings appeared on the membranes around the control magnetic dots (without Tween 20) compared to test membranes that were colored inside the magnetic dots.

Example XII
Synthesis of peptides by combinatorial chemistry

Figure 6:
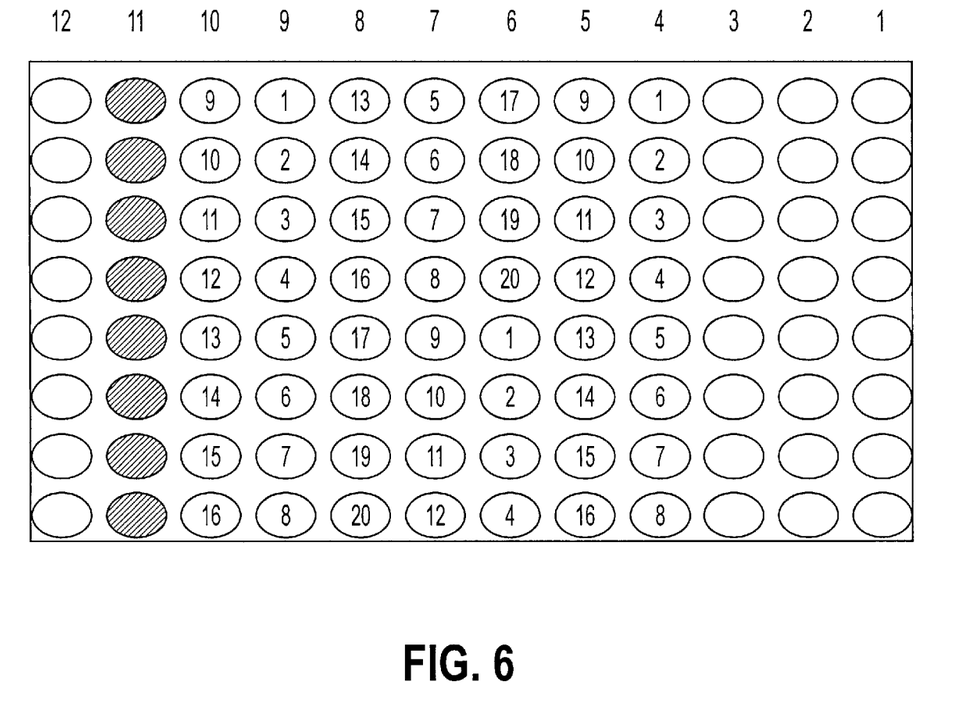
FIG. 6 shows a scheme for peptide synthesis by combinatorial chemistry.

A 96-well polypropylene assembly was prepared as in FIG. 6.

The column arrangement is as follows:

Column 1: 100 μl magnetic particle suspensions, each particle having attached thereto an amino acid having a blocked end;

Column 2: 100 μl of trifluoro-acetic acid in di-chloro-methane 50:50% (v/v);

Column 3: 100 μl of di-isopropyl ethyl amino;

Columns 4–6:in each well is present one of the 20 naturally occurring amino acids (marked arbitrarily by numbers 1–20) with dicyclohexylcarbodiimide;

Column 11: 100 HF and the final peptidic product;

Column 12: isolated magnetic particles.

The synthesis steps are as follows:

(a) The magnetic particles in Column 1 are already attached to a first amino acid having a blocked end. With a multi-pin magnetic device having 8 pins corresponding in size and spacing to the size of the wells, all 8-rows of column 1 are picked at once, transferred to column 2 and released into the wells for the release of the blocked amino acids by the tri-fluoro-acetic acid.

(b) the particles are then picked again by the multi-pin device and transferred to column 3.

(c) From column 3 the particles are again moved to column 4 so that a di-peptide is formed.

(d) Steps (a)–(c) are repeated again but with rows 5–10 instead of row 4, in order to receive newly synthesized peptide 3–10 amino acids long.

(e) When a peptide of a desired length is obtained, it is transferred to column 11 having an agent capable of breaking the linkage between the peptide and the magnetic particle.

(f) The free particles are picked from column 11 and transferred to column 12 for further use.

Alternatively, it is possible to take peptides still bound to magnetic particles and transfer them to a membrane for further processing, for example, for the creation of a peptidic map.

As a result of the process in each of the eight rows of column 11 there is a peptide of the same desired length having an amino acid sequence which is different than that of the peptides in the other rows.

What is claimed is:

1. A method for separating at least one specific species of biological entities from a sample solution, said specific species constitute a first member of a pair forming group, the method comprising:

(a) contacting the sample with a matrix of magnetic particles formed on a first substrate, the magnetic particles being coupled to at least one species of a second member of the pair forming group which specifically binds to said at least one species of biological entities;

(b) collecting magnetic particles from a desired location in the matrix; and (c) rearranging the collected particles on another substrate in order to form a new matrix of magnetic particles.

2. A method according to claim 1, wherein the biological entities are selected from the group consisting of nucleic acid sequences, proteins, hormones, antibiotics, cells and virions.

3. A method according to claim 1, wherein said new matrix of magnetic particles is a high density magnetic matrix.

4. A method according to claim 1, wherein the magnetic particles are arranged in a matrix of 96-dots, corresponding to a 96-pin and 96-well standard format.

5. A method according to claim 1, wherein the magnetic particles are coupled to at least two species of the second members of the pair forming group, wherein all magnetic particles coupled to the same species of the second member are present in the same location in the matrix, which location is discrete from the location of magnetic particles coupled to other species of the second member.

6. A method according to claim 1, wherein the new matrix is processed in order to obtain a detectable label at the locations of the separated biological entities.

7. A method according to claim 6, wherein said processing is carried out by contacting the matrix with a reaction mixture comprising antibodies or oligonucleotides bearing detectable labels and capable of specifically binding to the biological entities.

8. A method according to claim 6, wherein said processing is carried out by staining the matrix with dye or reacting the matrix with enzymes.

9. A method according to claim 1, wherein the biological entities are nucleic acid sequences and wherein by said method sequencing by hybridization is achieved.

10. A method according to claim 1, wherein the matrix is formed on a flat substrate.

11. A method according to claim 10, wherein the substrate is a glass, plastic or metal board and the magnetic particles are immobilized on the substrate by means of a magnet, placed behind said substrate.

12. A method according to claim 1, wherein the substrate is a sheet capable of absorbing or adsorbing the magnetic particles.

13. A method according to claim 1, wherein the substrate is a gel.

14. A method according to claim 1, wherein the matrix is formed in an array of liquid-holding wells placed on a magnet.

15. A method according to claim 1, wherein the first substrate is an array of liquid-holding wells and another substrate is a membrane.

* * * * *